US00PP20017P3

(12) United States Plant Patent
Nickson

(10) Patent No.: US PP20,017 P3
(45) Date of Patent: May 26, 2009

(54) *CYNODON DACTYLON* PLANT NAMED 'GRAND PRIX'

(50) Latin Name: *Cynodon dactylon*
Varietal Denomination: Grand Prix

(76) Inventor: David Nickson, 29 Fleetwood Crescent, Frankston South, Victoria (AU), 3199

( * ) Notice: Subject to any disclaimer, the term of this patent is extended or adjusted under 35 U.S.C. 154(b) by 0 days.

(21) Appl. No.: 11/786,390

(22) Filed: Apr. 11, 2007

(65) Prior Publication Data

US 2008/0271217 P1 Oct. 30, 2008

(51) Int. Cl.
*A01H 5/00* (2006.01)

(52) U.S. Cl. ..... Plt./389
(58) Field of Classification Search ..... Plt./389
See application file for complete search history.

(56) References Cited

U.S. PATENT DOCUMENTS

PP6,278 P 9/1988 McMaugh et al.

OTHER PUBLICATIONS

Australian Plant Varieties Journal; Quarter Four 2005; vol. 18 No. 4, pp. 1, 96–104 (10 pages total).*
RJ & ML Riley Pty Ltd, 'Riley's Evergreen', Plant Varieties Journal, 1999, vol. 12, No. 3.
Enviroseeds Pty Ltd, 'Hatfield', Plant Varieties Journal, 2003, vol. 16, No. 4.
David Nickson, 'Winter Gem', Plant Varieties Journal, 2005, vol. 18, No. 4, date of publication: Mar. 1, 2006.

* cited by examiner

*Primary Examiner*—S. B. McCormick Ewoldt
(74) *Attorney, Agent, or Firm*—Ostrager Chong; Flaherty & Broitman P.C.

(57) ABSTRACT

The new variety of *Cynodon dactylon* named 'Grand Prix' exhibiting a dense stolon mat, fine textured leaves, low production of seed heads and wear tolerance.

1 Drawing Sheet

FIELD OF THE INVENTION

The present invention relates to a new and distinct variety of *Cynodon dactylon* (L.) Pers. plant, botanically known as *Cynodon dactylon,* and hereinafter referred to by the cultivar name 'Grand Prix'.

*Cynodon dactylon* is a member of the grass family generally used for turf and has the common name of green couch grass in Australia and Bermudagrass in the United States. 'Grand Prix' has demonstrated high turf quality, dense matting, improved wear tolerance and low seed head density amongst other unique features. This new grass is useful for golf course fairways, tees, residential and commercial lawns, sports fields, recreational areas, such as parks, and other similar applications.

BACKGROUND OF THE INVENTION

The new cultivar 'Grand Prix' is a selection from a cross between 'Wintergreen' (female parent) and 'Couch 5' (male parent) in 1998. 'Couch 5' is also known as C5. The resultant seeds of that cross were germinated and 150 seedlings were observed during 1998 and 1999. During the summer of 1999 to 2000, seedling plants were culled based on their shoot density, leaf texture, internode length and colour. The remaining 20 plants were planted in pots at at Pakenham, Victoria, Australia in Spring of 2000. The final selection of Seedling 12 in 2002 was based on shoot density, leaf colour, turf quality and reduced thatch accumulation.

To ensure the unique characteristics of the new cultivar remained stable and reproduced true-to-type, the original selected plant was asexually propagated by dividing the stolon into nodal cuttings at Pakenham, Victoria, Australia and has been multiplied through four vegetative expansions without showing any discernible off types.

Internode length and branching, length and width of the leaf blade, inflorescence raceme length and culm length were characteristics which were used for determine the most similar varieties of common general knowledge. 'C1', 'Hatfield', 'Riley's Evergreen', 'Winter Gem' and 'Wintergreen' were identified.

'C1' is the variety not protected by any plant variety rights and is sold under the Australian registered trade mark Legend®. 'Hatfield' is disclosed in Australian PBR No. 2565. 'Riley's Evergreen' is disclosed in Australian PBR No. 1506 and is sold under the Australian registered trade mark Conquest®. 'Winter Gem' is disclosed in Australian PBR No. 3132 and 'Wintergreen' is disclosed in U.S. Plant Pat. No. 6,278.

SUMMARY OF THE INVENTION

Plants of the new cultivar 'Grand Prix' have not been observed under all possible environmental conditions. The phenotype may differ somewhat with variations in environment such as temperature, light intensity and day length without, however, any variance in genotype.

The following traits have been repeatedly observed and are determined to be the unique characteristics of 'Grand Prix'. These characteristics in combination distinguish 'Grand Prix' as a new and distinct cultivar:

1. low inflorescence density,
2. short inflorescence spike length;
3. short leaf blade length,
4. medium leaf blade width,
5. short stolon internode length,
6. thick stolon These characteristics contribute the advantageous features in 'Grand Prix' of forming a dense stolon mat that has finely textured leaves, low numbers of seed heads reducing the mowing requirement and improving wear tolerance of the turf.

The new variety is propagated vegetatively by sod, plugs, sprigs, tillers, rhizomes or stolons. Vegetative propagation has established that the characteristics have been passed through at least four generations without showing any discernible off types.

DETAILED BOTANICAL DESCRIPTION

Figure 1:
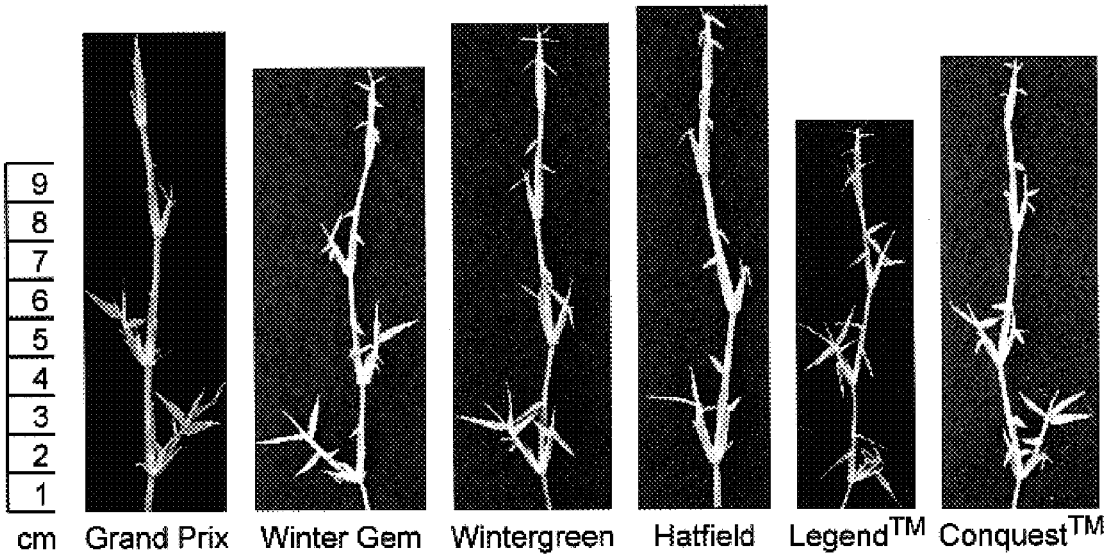
FIG. 1 shows a comparison of the new variety (left) with comparators (from left to right) 'Winter Gem', 'Wintergreen', 'Hatfield', 'Legend®' (C1) and 'Conquest®' (Riley's Evergreen).

Latin name of the genus and species of the plant claimed: The present invention relates to the genus and species *Cynodon dactylon* (L.) Pers, Variety denomination: 'Grand Prix'.

Plants of the cultivar 'Grand Prix' have not been observed under all possible environmental conditions. The phenotype may vary somewhat with variations in environment such as temperature, light intensity and day length without, however, any variance in genotype.

1. Origin and Breeding

'Grand Prix' resulted from controlled pollination followed by selection. The new variety is a selection from a cross between 'Wintergreen' (female parent) and 'Couch 5' (male parent). 'Couch 5' also known as C5. was a selection from an earlier series of crosses by the breeder between 'Wintergreen' and a number of *Cynodon dactylon* accessions, which were collected by the breeder from the Mornington Peninsula area of Victoria, Australia between 1986 and 1990. C5 was an experimental breeding line, and was not subsequently reserved as vegetative germplasm. Living material of C5 is no longer in existence.

Following the crossing of 'Couch 5' and 'Wintergreen' in 1998, the resultant seed was germinated on moist blotting paper. Individual seedlings, a total of 150 in number, were planted into 150 mm pots and these plants observed during 1998 and 1999. During the summer of 1999–2000, the majority of the seedling plants were culled on the basis of their shoot density, leaf texture, internode length, and colour. In the spring of 2000, the remaining 20 potted seedlings were planted individually into $4m^2$ plots at a turf farm at Pakenham, Victoria, Australia and allowed to expand fully across these plots.

The final selection of Seedling 12 (later designated DN12) in late 2002 was based on shoot density, leaf colour, turf quality, and reduced thatch accumulation as expressed in these plots. The original selected plant was asexually propagated vegetatively by dividing the stolons into nodal cuttings which were struck on the turf farm at Pakenham. The selected plant has been multiplied through at least four (4) such vegetative expansions without showing any discernible off types.

2.Characteristics

The description of the variety is taken from the comparative trials conducted in the period of May 31, 2005 –Dec. 16, 2005 at Cleveland, Queensland, Australia (Latitude 27°32' South, Longitude 153°15' East, elevation 25 masl). The characteristics of the new variety are as follows, with all R.H.S. colour chart numbers referring to 2001 edition.

Classification: *Cynodon dactylon* 'Grand Prix'.

Parentage: Cross between 'Wintergreen' (female parent) and 'Couch 5' (male parent).

Propagation. Vegetative propagation (asexual) by sod, plugs, sprigs, tillers and pieces of rhizomes or stolons.

Growth habit: Type low growing, creeping, dense mat-forming, spreading laterally by stolons and rhizomes.

Leaf blade: Shape linear-triangular, length short, width medium.

Stolon: Compound nodes with up to 3 leaves, internode length short-medium, internode thickness medium-thick.

Culms: Length short.

Ligule: Dense row of short white hairs.

Inflorescence: Digitate with (2-)3–4 short spicate racemes.

Vegetative leaf:

*Mean blade length on fourth leaf of flowering tillers.*—34.41 mm.

*Mean blade length on fourth node from stolen tip.*—3.03 mm.

*Mean sheath width on fourth leaf of flowering tillers.*—2.61 mm.

*Mean blade width on fourth node from stolen tip.*—1.46 mm.

*Mean sheath length on fourth leaf of flowering tillers.*—15.42 mm.

*Mean blade length on fourth node from stolen tip.*—9.16 mm.

Inflorescence characters:

*Mean length of peduncle on flowering tiller.*—69.29 mm.

*Mean diameter of peduncle on flowering tiller.*—0.53 mm.

*Mean flag leaf length on flowering tiller.*—19.24 mm.

*Mean flag leaf width on flowering tiller.*—2.01 mm.

*Mean length of inflorescence spikes.*—34.15 mm.

*Mean number of spikes per inflorescence.*—3.45. Mean inflorescence density (number per $0.01m^2$) 16.10.

Colour notations, vegetative characters, based The R.H.S. Colour Chart (edition 2001):

*Leaf blade color.*—Dark Green 137B (Taken at end of Spring).

*Stolon colon.*—Grey-brown N199A (Taken at end of Spring when exposed to sunlight).

Wear Tolerance: Very high.

Disease susceptibility: The new variety has not shown any unusual susceptibility to diseases or diseases when compared to the species.

3. Comparative Trial

Conditions: Individual propagules were grown in 40×40 mm tubes from Mar. 8, 2005. All varieties were planted on a 1 m×1 m spacing in ferrosol soil (Isbell, R. F. (2002) 'The Australian Soil Classification'. Revised Edition. CSIRO Publishing. Collingwood, Victoria. Australia) on May 31, 2005. The plants were not defoliated and weed control by pre-emergence oxadiazon was conducted on May 31, 2005 and Aug. 10, 2005. Pest and disease control was conducted with cyfluthrin (armyworm) on (Jun. 7, 2005, with dimethoate (couch tip maggot) on Oct. 17, 2005 and with propiconazole (leaf spot) on Oct. 17, 2005. Nutrition was maintained by slow release starter fertiliser (18-10-9) from May 31, 2005.

Trial Design: The trials composed of thirty (30) plants per variety, with five (5) plants per plot in six (6) randomised blocks.

Measurements: Four (4) diameter of spread measurements per plant were taken on Jul. 12, 2005, Jul. 24, 2005, Aug. 9, 2005, Aug. 23, 2005, Sep. 6, 2005 and the final at 173 days on Sep. 20, 2005. Two (2) stolon leaf, internode and colour measurements were taken on spaced plants on Nov. 15,–Nov. 21, 2005. Two (2) shoot and inflorescence measurements were taken on Dec. 14–16, 2005 on spaced plants. The inflorescence density (0.01 $m^2$) per plant was collected Dec. 19–23, 2005.

In order to choose the trial comparators, the following characteristics used for grouping varieties to identify the most similar variety of common knowledge:

| Organ/Plant Part | Context | State of Expression in Group of Varieties |
|---|---|---|
| Stolon | internode length | short to medium |
| Stolon | internode branching | medium to strong |
| Leaf blade | length | medium to long |
| Leaf blade | width | medium |
| Inflorescence | raceme length | short |
| Culm | length | short |

The most similar varieties of common knowledge identified (VCK).

| Name | Comments |
|---|---|
| 'C1' | 'C1' is the closest Variety of Common Knowledge. Material planted was the truest to type available of this cultivar. This variety is marketed as Legend ® |
| 'Riley's Evergreen' | The variety is marketed as Conquest ® |
| 'Winter Gem' | Planting material obtained from the breeder, derived from the same cross as 'Grand Prix' |
| 'Hatfield' | Planting material obtained from thc breeder |
| 'Wintergreen' | Samples were obtained from breeder Peter McMaugh's 'Wintergreen' nursery block that has been planted for 7-8 years. This material is the truest to type available for this cultivar. |

Table 1 shows the characteristics of the chosen comparative varieties and Tabe lists the statistical measurements.

TABLE 1

| 'Grand Prix' | 'C1' | 'Hatfield' | 'Riley's Ever-green' | 'Winter-Gem' | 'Winter-green' |
|---|---|---|---|---|---|
| PLANT: GROWTH TYPE | | | | | |
| Creeping | Creeping | Creeping | Creeping | Creeping | Creeping |
| PLANT: HEIGHT | | | | | |
| Short | Short | Short | Short | Short | Short |
| LEAF: PRIMARY COLOUR (RHS COLOUR CHART) | | | | | |
| 137B | 137B | 137B | 137B | 137B | 137B |
| INFLORESCENCE SPIKES: MAXIMUM NUMBER | | | | | |
| 4 | 5 | 5 | 5 | 4 | 5 |
| INFLORESCENCE SPIKES: MINIMUM NUMBER | | | | | |
| 2 | 3 | 3 | 2 | 3 | 3 |
| STOLON: EXPOSED COLOUR (RHS COLOUR CHART) | | | | | |
| N199A | N199A | N199A | N199A | 148A | N199B |

TABLE 1-continued

| 'Grand Prix' | 'C1' | 'Hatfield' | 'Riley's Ever-green' | 'Winter-Gem' | 'Winter-green' |
|---|---|---|---|---|---|
| PLANT: LONGEVITY | | | | | |
| perennial | perennial | perennial | perennial | perennial | perennial |
| PLANT: TYPE | | | | | |
| mat-forming | mat-forming | mat-forming | mat-forming | mat-forming | mat-forming |
| PLANT: PROLIFERATION | | | | | |
| stolons and rhizomes | stolons and rhizomes | stolons and rhizomes | stolons and rhizomes | stolons and rhizomes | stolons and rhizomes |
| STOLON: INTERNODE LENGTH | | | | | |
| short to medium | short to medium | short to medium | short to medium | short to medium | short to medium |
| CULM: LENGTH | | | | | |
| short | short | short | short | short | short |
| LEAF BLADE: LENGTH | | | | | |
| short | short to medium | short | short | short to medium | short to medium |
| INFLORESCENCE: PEDUNCLE LENGTH | | | | | |
| short to medium | short | short | short | short to medium | short to medium |
| STOLON: COMPOUND NODES | | | | | |
| with = 3 leaves | with = 3 leaves | with = 3 leaves | with = 3 leaves | with = 3 leaves | with = 3 leaves |
| STOLON: INTERNODE THICKNESS | | | | | |
| medium to thick | medium | medium | medium | medium | medium |
| LEAF BLADE: WIDTH | | | | | |
| medium | medium | medium | medium | medium | medium |
| LEAF BLADE: SHAPE | | | | | |
| linear-triangular | linear-triangular | linear-triangular | linear-triangular | linear-triangular | linear-triangular |
| LIGULE: TYPE | | | | | |
| hairs | hairs | hairs | hairs | hairs | hairs |
| LIGULE: HAIR PLACEMENT | | | | | |
| dense | dense | dense | dense | dense | dense |
| INFLORESCENCE: SHAPE | | | | | |
| digitate | digitate | digitate | digitate | digitate | digitate |
| INFLORESCENCE: BRANCHING | | | | | |
| spicate | spicate | spicate | spicate | spicate | spicate |
| INFLORESCENCE: RACEME LENGTH | | | | | |
| short | short | short | short | short | short |
| INFLORESCENCE: DENSITY | | | | | |
| low | medium to high | medium to high | medium to high | medium to high | medium to high |
| LIGULE: SIZE | | | | | |
| short | short | short | short | short | short |

TABLE 2

| | 'Grand Prix' | 'Winter Gem' | 'Winter-green' | 'Hat-field' | 'C1' | 'Riley's Ever-green' |
|---|---|---|---|---|---|---|
| MEAN PLANT DIAMETER AFTER 173 DAYS (cm) | | | | | | |
| mean | 72.1 | 40.3 | 78.1 | 64.5 | 69.9 | 47.2 |
| std deviation | 12.1 | 6.2 | 20.4 | 16.2 | 8.7 | 10.3 |
| LSD/sig | 12.2 | P ≦ 0.05 | ns | ns | ns | P ≦ 0.05 |
| FIRST STOLON NODE WITH A SECOND LATERAL BRANCH (SPACED PLANTS) | | | | | | |
| mean | 0.80 | 0.80 | 0.82 | 0.50 | 1.25 | 1.23 |
| std deviation | 0.18 | 0.17 | 0.19 | 0.15 | 0.26 | 0.10 |
| LSD/sig | 0.22 | ns | ns | P ≦ 0.05 | P ≦ 0.05 | P ≦ 0.05 |
| FIRST STOLON NODE WITH A THIRD LATERAL BRANCH (SPACED PLANTS) | | | | | | |
| mean | 1.08 | 0.98 | 1.28 | 1.02 | 2.02 | 2.18 |
| std deviation | 0.10 | 0.04 | 0.21 | 0.10 | 0.32 | 0.32 |
| LSD/sig | 0.25 | ns | ns | ns | P ≦ 0.05 | P ≦ 0.05 |
| FIRST STOLON NODE WITH A FOURTH LATERAL BRANCH (SPACED PLANTS) | | | | | | |
| mean | 1.65 | 1.38 | 1.95 | 1.22 | 3.23 | 3.33 |
| std deviation | 0.36 | 0.12 | 0.35 | 0.34 | 0.50 | 0.32 |
| LSD/sig | 0.36 | ns | ns | P ≦ 0.05 | P ≦ 0.05 | P ≦ 0.05 |
| FIRST STOLON NODE WITH A FIFTH LATERAL BRANCH (SPACED PLANTS) | | | | | | |
| mean | 2.45 | 1.98 | 2.72 | 1.52 | 3.95 | 3.97 |
| std deviation | 0.45 | 0.26 | 0.43 | 0.36 | 0.48 | 0.44 |
| LSD/sig | 0.40 | P ≦ 0.05 | ns | P ≦ 0.05 | P ≦ 0.05 | P ≦ 0.05 |
| FIRST STOLON NODE WITH A SIXTH LATERAL BRANCH (SPACED PLANTS) | | | | | | |
| mean | 2.83 | 2.68 | 3.65 | 2.25 | 4.20 | 4.73 |
| std deviation | 0.22 | 0.17 | 0.75 | 0.37 | 0.48 | 0.45 |
| LSD/sig | 0.54 | ns | P ≦ 0.05 | P ≦ 0.05 | P ≦ 0.05 | P ≦ 0.05 |
| LENGTH OF FOURTH INTERNODE (mm) FROM STOLON TIP | | | | | | |
| mean | 33.27 | 30.51 | 44.68 | 44.88 | 49.20 | 41.73 |
| std deviation | 1.88 | 1.36 | 2.88 | 2.66 | 4.04 | 1.67 |
| LSD/sig | 3.17 | ns | P ≦ 0.05 | P ≦ 0.05 | P ≦ 0.05 | P ≦ 0.05 |
| DIAMETER OF FOURTH INTERNODE (mm) FROM STOLON TIP | | | | | | |
| mean | 1.75 | 1.36 | 1.41 | 1.52 | 1.59 | 1.28 |
| std deviation | 0.05 | 0.06 | 0.04 | 0.09 | 0.13 | 0.06 |
| LSD/sig | 0.09 | P ≦ 0.05 | P ≦ 0.05 | P ≦ 0.05 | P ≦ 0.05 | P ≦ 0.05 |
| LENGTH OF LEAF SHEATH (mm) ON FOURTH VISIBLE NODE FROM STOLON TIP | | | | | | |
| Mean | 9.16 | 7.40 | 9.84 | 10.74 | 10.26 | 7.30 |
| std deviation | 0.61 | 0.32 | 0.63 | 0.69 | 0.47 | 0.26 |
| LSD/sig | 0.63 | P ≦ 0.05 | P ≦ 0.05 | P ≦ 0.05 | P ≦ 0.05 | P ≦ 0.05 |
| LENGTH OF LEAF BLADE (mm) ON FOURTH VISIBLE NODE FROM STOLON TIP | | | | | | |
| mean | 3.03 | 3.28 | 8.00 | 6.39 | 7.97 | 4.91 |
| std deviation | 0.75 | 0.31 | 2.00 | 1.57 | 1.88 | 1.01 |
| LSD/sig | 1.21 | ns | P ≦ 0.05 | P ≦ 0.05 | P ≦ 0.05 | P ≦ 0.05 |
| WIDTH OF LEAF BLADE (mm) ON FOURTH VISIBLE NODE FROM STOLON TIP | | | | | | |
| mean | 1.46 | 1.35 | 2.02 | 1.85 | 2.31 | 1.77 |
| std deviation | 0.20 | 0.10 | 0.21 | 0.21 | 0.26 | 0.13 |
| LSD/sig | 0.17 | ns | P ≦ 0.05 | P ≦ 0.05 | P ≦ 0.05 | P ≦ 0.05 |
| LENGTH:WIDTH RATIO OF LEAF BLADE ON FOURTH VISIBLE NODE FROM STOLON TIP | | | | | | |
| mean | 1.89 | 2.37 | 3.80 | 3.34 | 3.31 | 2.66 |
| std deviation | 0.19 | 0.24 | 0.72 | 0.46 | 0.53 | 0.36 |
| LSD/sig | 0.44 | P ≦ 0.05 | P ≦ 0.05 | P ≦ 0.05 | P ≦ 0.05 | P ≦ 0.05 |
| LENGTH OF SHEATH (mm) ON FLAG LEAF ON FLOWERING TILLERS | | | | | | |
| mean | 53.03 | 63.70 | 63.93 | 56.27 | 57.33 | 48.27 |
| std deviation | 4.25 | 8.17 | 4.14 | 2.67 | 4.26 | 2.92 |
| LSD/sig | 5.58 | P ≦ 0.05 | P ≦ 0.05 | ns | ns | ns |
| LENGTH OF BLADE (mm) ON FLAG LEAF ON FLOWERING TILLERS | | | | | | |
| mean | 19.24 | 11.86 | 18.16 | 16.52 | 14.76 | 11.52 |
| std deviation | 4.87 | 3.60 | 4.08 | 3.02 | 1.54 | 1.49 |
| LSD/sig | 3.92 | P ≦ 0.05 | ns | ns | P ≦ 0.05 | P ≦ 0.05 |
| WIDTH OF BLADE (mm) ON FLAG LEAF ON FLOWERING TILLERS | | | | | | |
| mean | 2.01 | 1.24 | 1.55 | 1.55 | 1.59 | 1.27 |
| std deviation | 0.61 | 0.13 | 0.16 | 0.09 | 0.13 | 0.07 |
| LSD/sig | 0.30 | P ≦ 0.05 | P ≦ 0.05 | P ≦ 0.05 | P ≦ 0.05 | P ≦ 0.05 |
| LENGTH:WIDTH RATIO OF FLAG LEAF BLADE ON FLOWERING TILLERS | | | | | | |
| mean | 10.33 | 8.97 | 11.35 | 10.52 | 9.20 | 8.75 |
| std deviation | 2.09 | 1.87 | 2.02 | 1.61 | 1.12 | 0.93 |
| LSD/sig | 2.07 | ns | ns | ns | ns | ns |
| LENGTH OF SHEATH (mm) ON FOURTH LEAF ON FLOWERING TILLERS | | | | | | |
| mean | 15.42 | 16.27 | 17.93 | 16.94 | 16.00 | 14.67 |
| std deviation | 1.88 | 3.12 | 1.16 | 1.16 | 1.05 | 1.05 |
| LSD/sig | 2.14 | ns | P ≦ 0.05 | ns | ns | ns |
| LENGTH OF BLADE (mm) ON FOURTH LEAF ON FLOWERING TILLERS | | | | | | |
| mean | 34.41 | 29.93 | 40.34 | 33.77 | 26.97 | 29.26 |
| std deviation | 3.93 | 5.92 | 7.93 | 3.25 | 3.82 | 5.11 |
| LSD/sig | 6.46 | ns | ns | ns | ns | ns |
| WIDTH OF BLADE (mm) ON FOURTH LEAF ON FLOWERING TILLERS | | | | | | |
| mean | 2.61 | 2.22 | 2.60 | 2.50 | 2.53 | 2.17 |
| std deviation | 0.14 | 0.14 | 0.12 | 0.07 | 0.17 | 0.12 |
| LSD/sig | 0.14 | P ≦ 0.05 | ns | ns | ns | P ≦ 0.05 |

TABLE 2-continued

| | 'Grand Prix' | 'Winter Gem' | 'Winter-green' | 'Hat-field' | 'C1' | 'Riley's Ever-green' |
|---|---|---|---|---|---|---|
| LENGTH:WIDTH RATIO OF FOURTH LEAF BLADE ON FLOWERING TILLERS | | | | | | |
| mean | 13.26 | 11.17 | 15.47 | 13.56 | 10.76 | 13.53 |
| std deviation | 1.35 | 2.23 | 2.56 | 1.32 | 1.75 | 2.11 |
| LSD/sig | 2.47 | ns | ns | ns | 0.05 | ns |
| LENGTH OF PEDUNCLE (mm) ON FLOWERING TILLERS | | | | | | |
| mean | 69.29 | 106.94 | 104.49 | 78.92 | 79.83 | 84.42 |
| std deviation | 5.90 | 16.43 | 5.85 | 4.85 | 8.24 | 8.94 |
| LSD/sig | 10.47 | P ≦ 0.05 | P ≦ 0.05 | ns | P ≦ 0.05 | P ≦ 0.05 |
| DIAMETER OF PEDUNCLE (mm) ON FLOWERING TILLERS | | | | | | |
| mean | 0.53 | 0.48 | 0.63 | 0.55 | 0.59 | 0.50 |
| std deviation | 0.04 | 0.03 | 0.05 | 0.04 | 0.03 | 0.04 |
| LSD/sig | 0.04 | P ≦ 0.05 | P ≦ 0.05 | ns | P ≦ 0.05 | ns |
| MEAN LENGTH OF SPIKES (mm) | | | | | | |
| mean | 34.15 | 42.27 | 44.45 | 44.14 | 41.22 | 32.02 |
| std deviation | 2.32 | 6.00 | 1.54 | 1.81 | 2.63 | 2.18 |
| LSD/sig | 3.79 | P ≦ 0.05 | P ≦ 0.05 | P ≦ 0.05 | P ≦ 0.05 | ns |
| NUMBER OF SPIKES PER INFLORESCENCE | | | | | | |
| mean | 3.45 | 3.72 | 4.00 | 4.07 | 3.88 | 3.17 |
| std deviation | 0.00 | 0.00 | 0.41 | 0.55 | 0.41 | 0.82 |
| LSD/sig | 0.25 | P ≦ 0.05 | P ≦ 0.05 | P ≦ 0.05 | P ≦ 0.05 | P ≦ 0.05 |
| INFLORESCENCE DENSITY (NUMBER PER 0.1 $M^2$): 23 DEC. 2005 (UNMOWN SWARDS) | | | | | | |
| mean | 16.10 | 111.90 | 94.90 | 112.50 | 109.50 | 118.90 |
| std deviation | 7.45 | 46.66 | 26.34 | 19.87 | 57.16 | 69.88 |
| LSD/sig | 57.05 | P ≦ 0.05 | P ≦ 0.05 | P ≦ 0.05 | P ≦ 0.05 | P ≦ 0.05 |
| MAXIMUM NUMBER OF SPIKES PER INFLORESCENCE | | | | | | |
| | 4 | 4 | 5 | 5 | 5 | 5 |
| MINIMUM NUMBER OF SPIKES PER INFLORESCENCE | | | | | | |
| | 2 | 3 | 3 | 3 | 3 | 2 |
| STOLON COLOUR EXPOSED TO SUNLIGHT (RHS, 2001) | | | | | | |
| | N199A | 148A | N199B | N199A | N199A | N199A |
| LEAF COLOUR (RHS, 2001) | | | | | | |
| | 137B | 137B | 137B | 137B | 137B | 137B |

Statistical differences among the cultivars were determined according to standard statistical tests.

After 173 days, 'Grand Prix' demonstrated a similar rate of lateral spread to all varieties except a 'Riley's Evergreen' and 'Winter Gem' which were relatively slower growing. The length of the fourth stolon internode of the new variety was relatively short with only 'Winter Gem' being smaller but not significantly. Short internodes enable greater shoot density as the shoots are produced from nodes on the stolons that are closer together forming a tight mat. In combination with its prostrate spreading habit, 'Grand Prix' forms a dense turf with good ground coverage.

The leaf length on the fourth internode of 'Grand Prix' was shorter than all comparators and the leaf width was less than the other comparators, except for 'Winter Gem'. The new variety significantly had the lowest leaf length:width ratio and as such these leaf measurements indicate that 'Grand Prix' has fine textured leaves.

Of particular note, seed head production by 'Grand Prix' was significantly lower than all the other comparative varieties. This is shown by the inflorescence density where the new variety had an average 16.10 inflorescences per 0.1 $m^2$ area compared to the comparators having over 90. The very low seed head production of 'Grand Prix' provides an attractive appearance to the turf and reduces the need mow as regularly as the other varieties. The inflorescence spike length is similar to 'Riley's Evergreen', but significantly shorter against all comparators. Short spikes are less intrusive visually in the turf.

The diameter of the fourth stolon internode of 'Grand Prix' is significantly larger than that of all the comparators. This characteristic assists in providing wear tolerance as a thicker stolon is able to provide more resistance to wear stress.

A wear trial was conducted at Cleveland, Queensland, Australia. 'Grand Prix' showed significantly greater tolerance to weekly and fortnightly wear treatments applied with a Brinkman Traffic Simulator (Cockerham, S. T. and D. J. Brinkman. (1989). A simulator for cleated-shoe sports traffic on turfgrass research plots. California Turfgrass Culture 39 (3, 4), 9-12.) fitted with smooth rubber rollers rotating at different speeds to give a scuffing action. 'Grand Prix' maintained higher turf quality and a lower percentage of bare ground under wear than the other cultivars. Table 3 shows the wear tolerance ratings for seven *Cynodon dactylon* cultivars based on turf quality and percentage of bare ground 35 days after commencing weekly and fortnightly wear treatments. The wear test started Jul. 14, 2006 and the data presented in Table 3 was recorded Aug. 18, 2006 after 5 weeks of wear treatment. The varieties 'Princess' and 'JTI' were included in the wear trial, but are not considered to be similar varieties of common general knowledge to 'Grand Prix'.

TABLE 3

| | Wear | Turf Quality Rating (0-9) | | |
|---|---|---|---|---|
| Cultivar | Tolerance Rating | No Wear (Control) | Fortnightly Wear | Weekly Wear |
| Grand Prix | 1 | 7.8 | 5.0 | 4.1 |
| C1 | 2 | 6.8 | 3.6 | 3.4 |
| Riley's Evergreen | 3 | 6.3 | 3.4 | 3.0 |
| Wintergreen | 4 | 6.4 | 2.9 | 2.3 |
| Princess | 5 | 7.4 | 3.3 | 1.9 |
| Hatfield | 6 | 6.5 | 2.5 | 1.4 |
| JT1 | 7 | 6.0 | 1.4 | 1.1 |
| LSD (P = 0.05) | — | 0.8 | 0.9 | 0.7 |

| | Bare Ground (%) | | |
|---|---|---|---|
| Cultivar | No Wear (Control) | Fortnightly Wear | Weekly Wear |
| Grand Prix | 0.0 | 17.5 | 33.8 |
| C1 | 0.0 | 41.3 | 52.5 |
| Riley's Evergreen | 0.0 | 40.0 | 53.8 |
| Wintergreen | 0.0 | 47.5 | 66.3 |
| Princess | 0.0 | 47.5 | 75.0 |
| Hatfield | 0.0 | 50.0 | 78.8 |
| JT1 | 0.0 | 83.8 | 87.5 |
| LSD (P = 0.05) | — | 22.2 | 13.4 |

Analyses of samples of leaf and thatch from this experiment showed higher Lignin, Neutral Detergent Fiber (NDF)

and Total Cell Wall (TCW) contents in 'Grand Prix' than in the other bermudagrass cultivars. Table 4 indicates the chemical analysis of structural components in samples of leaf and thatch taken from seven *Cynodon dactylon* cultivars mown to 25 mm. All results expressed as percentages (w/w) on a dry matter basis.

TABLE 4

| Cultivar | Lignin (%) | TCW (%) | NDF (%) |
|---|---|---|---|
| Grand Prix | 5.83 | 38.62 | 66.55 |
| C1 | 4.73 | 36.95 | 63.58 |
| Riley's Evergreen | 4.53 | 37.02 | 64.73 |
| Wintergreen | 4.38 | 35.97 | 64.23 |
| Princess | 5.28 | 35.20 | 62.75 |
| Hatfield | 4.15 | 34.82 | 61.68 |

TABLE 4-continued

| Cultivar | Lignin (%) | TCW (%) | NDF (%) |
|---|---|---|---|
| JT1 | 4.20 | 33.62 | 59.45 |
| LSD (P = 0.05) | 0.81 | 2.86 | 4.05 |

'Grand Prix' is a turf grass having distinguishing features from 'C1', 'Hatfield', 'Riley's Evergreen', 'Winter Gem' and 'Wintergreen'.

What is claimed is:

1. A new and distinct variety of *Cyondon dactylon* plant, substantially as described and illustrated herein, characterized particularly by a unique combination of morphological characters.

* * * * *